(12) United States Patent
Jacob

(10) Patent No.: US 6,440,391 B1
(45) Date of Patent: Aug. 27, 2002

(54) MANAGEMENT OF SNORING BY ORAL ADMINISTRATION OF DIMETHYL SULFONE

(75) Inventor: Stanley W. Jacob, Portland, OR (US)

(73) Assignee: Elstan Corporation, Portland, OR (US)

( * ) Notice: Subject to any disclaimer, the term of this patent is extended or adjusted under 35 U.S.C. 154(b) by 0 days.

(21) Appl. No.: 09/586,075

(22) Filed: Jun. 2, 2000

(51) Int. Cl.⁷ ................ A61K 31/10; A61K 31/045; A61K 9/12
(52) U.S. Cl. ............. 424/43; 514/709; 514/711; 514/724; 514/723; 514/736
(58) Field of Search .................. 514/709, 711, 514/923, 936, 942, 853, 724; 424/43

(56) References Cited

U.S. PATENT DOCUMENTS

| | | |
|---|---|---|
| 4,477,469 A | 10/1984 | Herschler |
| 4,863,748 A | 9/1989 | Herschler |
| 5,569,679 A | 10/1996 | Jacob |

OTHER PUBLICATIONS

Drug information Handbook, Lacy, Armstrong, Lipsy and Lance, Lexicomp, 1993, pp. 95, 384–385 and 375–676.*
"Snoring: Pathogenic, Clinical and Therapeutic Aspects", Principles and Practice of Sleep Medicine, Kryger et al, Editors 1989, pp. 494–500.
"The ABZzzzs of snoring", Post Graduate Medicine, (Sep. 1, 1992).
"The Sleep Apnoea/Hypopnoea Syndrome and Snoring", British Medical Journal, 1993, vol. 306:1057–60.

* cited by examiner

*Primary Examiner*—Michael G. Hartley
*Assistant Examiner*—M. Haghighatian
(74) *Attorney, Agent, or Firm*—Timothy J. Martin; Michael R. Henson; Mark H. Weygandt

(57) ABSTRACT

A method of managing snoring is provided by the instillation orally of a solution containing 1–20% methylsulfonylmethane by weight dissolved in water so as to cover the mucous membranes of the orophyrnx. Preferably, the solution has between 10%–15% by weight methylsulfonylmethane. The solution may be buffered, and/or a flavoring may be included. The method prefers that instillation occur as close to the sleep event as possible, and it should be at least within thirty (30) minutes to fifteen (15) minutes before a person retires for sleep. The solution may be introduced by spray or drop-wise, and a product packaging the solution in a suitable container is described.

13 Claims, 1 Drawing Sheet

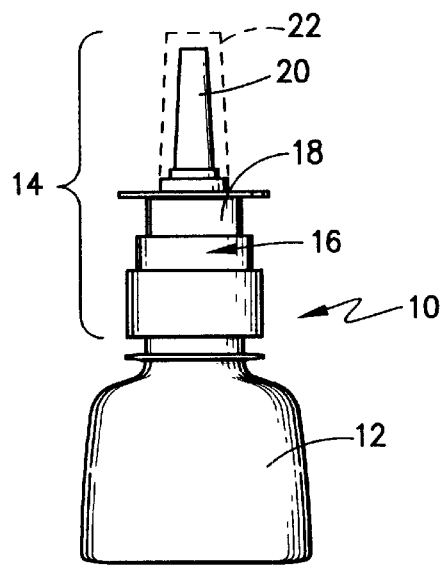
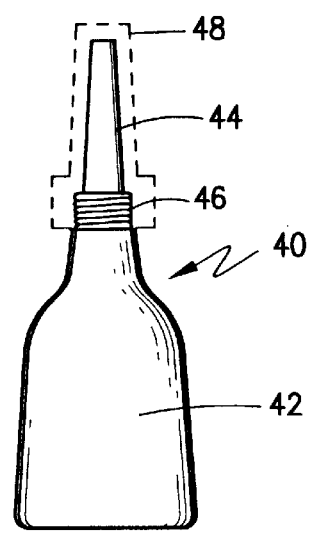
Fig.1
(PRIOR ART)
Fig.2
(PRIOR ART)
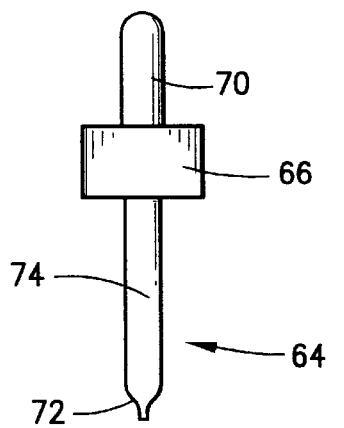
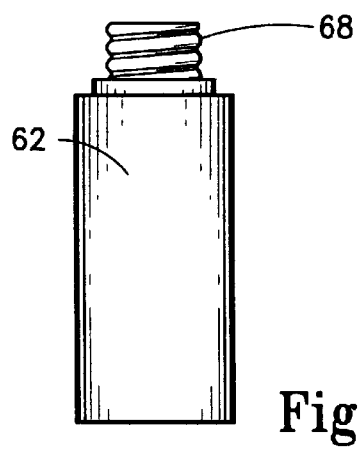
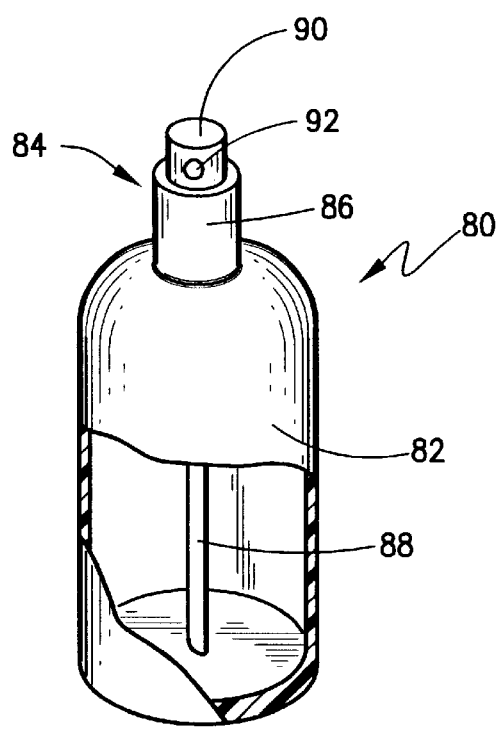
Fig.3
(PRIOR ART)
Fig.4
(PRIOR ART)

MANAGEMENT OF SNORING BY ORAL ADMINISTRATION OF DIMETHYL SULFONE

FIELD OF THE INVENTION

The present invention broadly concerns the management of snoring by reducing the incidence or magnitude thereof. More particularly, however, the present invention is directed to reducing or eliminating snoring by oral administration of compositions to the orophyrnx region of the throat. This invention directly concerns the method of managing snoring by contacting the mucous membranes of the orophyrnx with methylsulfonylmethane.

BACKGROUND OF THE INVENTION

Snoring is an inspiratory sound which arises during a person's sleep. Snoring is believed to be generally caused by the narrowing of the nasopharyngeal airway such that turbulent airflow during relaxed breathing vibrates the soft parts of the oropharyngeal passage, such as the soft pallet, the posterior faucial pillars of the tonsils and the uvula. Many causes for the narrowing of the nasal pharyngeal airway, especially during sleep, exist, as noted below.

Snoring afflicts a large segment of the population, and is a condition affecting both sexes of all ages. During wakefulness, a person is typically able to consciously maintain the nasal pharyngeal passageway in an open condition; however, with the onset of sleep, relaxation allows the nasopharyngeal passageway to restrict, and snoring results. It has been estimated that up to 45% of all adults snore occasionally with about 25% being habitual snorers. Snoring increases with age, and it has been observed that about 50% of men and 40% of women are habitual snorers by the age of 60. Lugaresi et al, "Snoring: Pathogenic, Clinical and Therapeutic Aspects", Reported in *Principles and Practice of Sleep Medicine* (Kryger et al, Editors 1989) at pp. 494–500.

A restricted nasopharyngeal passageway can occur anatomically. For example, in children, this often is caused by obstruction due to enlarged tonsils or adenoids. In adults, it is not unusual for the narrowing to be caused by obesity. Further anatomical narrowing can be simple a matter of genetics with some persons being predisposed towards a smaller nasopharyngeal cross-section. A reduced nasopharyngeal passageway may also be caused by a lack of muscle tone. Other anatomical conditions contributing to the narrowing of the nasal pharyngeal passageway include choanal atresia, chrono polyp, nasal septal deviation, nasal pharyngeal cyst, macroglossia, retrognathia and micrognathia, but these less common. Leung et al, "The ABZzzz's of Snoring", *Post Graduate Medicine* (Sep. 1, 1992).

Snoring may also be exacerbated by consuming either alcohol or drugs (such as tranquilizers, sleeping pills and antihistamines) prior to bedtime. Smoking can contribute to the incidence of snoring since cigarettes may irritate the mucus membranes of the upper airway causing swelling and increased mucus production.

Prior to 1994, there had been no report of successful pharmacologic management of snoring. Douglas, "The Sleep Apnoea/Hypopnoea Syndrome and Snoring", *DMJ*, Volume 306 (1993); Leung et al, "The ABZzzz's of Snoring", *Post Graduate Medicine* (Sep. 1, 1992). However, numerous management techniques have been described, depending upon the perceived cause of snoring. None of these treatments have proved completely adequate. Where snoring is caused or exacerbated by nasal allergy or an upper respiratory track infection, these conditions may be treated pharmacologically, but, as noted above, this is not deemed to be a pharmacologic management of the overall snoring condition.

A basic treatment simply involves having the patient sleep in the prone position or on his/her side. Sometimes this is stimulated by sewing a marble or other object into the back of the snorer's clothes. Where the patient is obese, treatment may be a program of weight loss. Along with these treatments, of course, is the recommendation that the patient avoid use of drugs, cigarettes or alcohol prior to bedtime so as to retard the loss of oropharyngeal muscle tone. Snoring can sometimes be managed by the use of an appliance. One example is a custom-made mouth-piece constructed to move the snorer's lower jaw forwardly, thus opening the airway. Another example is the use of a positive pressure generator and face mask. These machines pump air through a hose and nose/mouth face mask to keep air passages clear. Use of each of these devices, however, can cause the subject to have less restful sleep.

Another option for treating snoring is found with surgical techniques. In children whose snoring is caused by an enlarge adenoids, and adenoidtotomy is sometimes prescribed. Where tonsils are also enlarged, a tonsillectomy often accompanies surgery to the adenoids. In adults, uvulopalatopharyngoplasty may be recommended for habitual or heavy snorers. Here, the surgeon resects the uvula, the distal portion of the soft pallet, the anterior tonsillar pillars and the redundant lateral pharyngeal wall mucosa. The purpose of such surgery, of course, is to increase the size of the air passageway thereby allowing unobstructed movement of air through the pharynx. Rates of success of the uvulopalatopharyngoplasty are uncertain, with improvement reported to be in a range from 15% to 65%. Douglas, "The Sleep Apnoea/Hypopnoea Syndrome And Snoring", *British Medical Journal*, 1993, Vol. 306:1057–60. In some instances, surgical repair of a deviated nasal septum has been shown to improve snoring.

In my U.S. Pat. No. 5,569,679 issued Oct. 29, 1996 and entitled pharmacologic Management of Snoring, I describe the use of intranasal solutions containing methylsulfonylmethane (dimethyl sulfone) for the pharmacologic reduction of snoring. Solutions containing 1% to 20% of methylsulfonyl methane by weight were instilled as drops into the nasal cavity to saturate the mucous membranes of the nasal passageways. This treatment proved highly effective, but one difficulty encountered with this technique was that some individuals noted a slight burning sensation upon the instillation of the compound through the nasal route. While the '679 Patent teaches the addition of an analgesic to the compound the analgesic may not always relieve this burning sensation. While not health threatening and mild, the burning sensation may tend to reduce a person's willingness to administer the treatment.

Snoring, therefore, remains a serious problem for a large segment of the population. Not only is it a nuisance, but can itself indicate a more serious condition and, due to exhaustion resulting from lack of sleep, can cause other problems. For example, an association between snoring and hypertension has been found, and cardiac arrhythmia has been reported during sleep apnea attacks. Snoring patients with decreased pulmonary function have been shown to suffer from severe apnea. Not only is the risk of cessation of breathing a danger for snoring, lack of oxygen due to an obstructed nasopharyngeal passageway deprives the body of sufficient oxygen so that an oxygen desaturation arises. Lack of oxygen may cause the brain to rouse the sleeper just enough to take a breath without fully awaking. Since this may happen hundreds of times a night, the snorer does not get sufficient sleep. Moreover, being aroused from deep REM sleep on a repetitive basis may increase heart rate and blood pressure. Thus, snoring may increase the risk of heart attack and stroke, as noted above. Further, due to narcolepsy resulting from exhaustion can cause a lack of attention for the snorer during waking hours thus reducing productivity and even causing dangerous situations should the exhausted snorer operate machinery or vehicles.

Accordingly, there has been a long felt need for improved management techniques to reduce or eliminate snoring. Specifically, a long felt need has existed for methodology in treating snoring which is simple and safe to administer. There remains a need to provide a route for administration other than intranasally. The present invention is directed to management technique by contacting the mucous membranes of the orophyrnx with snore-reducing compounds.

SUMMARY OF THE INVENTION

It is an object of the present invention to provide a new and useful method for the management of snoring.

Another object of the present invention is to provide a safe and relatively effective treatment that can be self-administered by a snorer prior to retiring for sleep.

Yet another object of the present invention is to provide an inexpensive method to reduce the incidence and/or magnitude of snoring that is safe and relatively effective for use.

Still a further object of the present invention is to provide a method directed to the contacting the orophyrnx with methylsulfonylmethane (MSM) through the oral route as a management technique for snoring.

Still another object of the present invention is to provide a product in the form of a dispenser containing a methylsulfonylmethane composition which may be instilled by an applicator onto the back of the throat as a method of reducing or eliminating the instance of snoring.

According to the present invention, then, a method for managing snoring is provided by the step of instilling a solution orally through the mouth and onto the oropharnyx wherein the solution includes a carrier solvent containing an effective amount of methylsulfonylmethane as a solute therein. Preferably, the solvent is water, and the methylsulfonylmethane is dissolved therein within a range of 1% and 20% by weight, inclusively. The solvent may also be water and phosphate buffered saline mixed in equal ratios.

Preferably, approximately 10% to 15% by weight of methylsulfonylmethane is used, and the solution is instilled onto the oropharnyx as a spray or drop-wise. The solution may contain a flavoring compound, if desired. Examples of such flavoring compounds include menthol, mints (such as peppermint and spearmint), fruit flavors (such as cherry and apple) and the like. Regardless of the mechanism by which the solution is instilled, it is preferred that the solution be instilled within a period of fifteen (15) minutes to thirty (30) minutes before the patient retires for sleep. Moreover, an amount of solution should be instilled of a sufficient quantity to cover the mucous membranes of the patient's oropharnyx, that is, the uvula, the tonsils and the soft pallet. This typically is an amount on the order of 0.8 ml to 1.2 ml per nostril.

The present invention also includes a product which is adapted for use in treating snoring. Here, the product is a solution containing a solvent for methylsulfonylmethane and an amount of methylsulfonylmethane dissolved therein. The solution is then packaged in a container. The container includes an applicator associated therewith for instilling the solution orally within a patient's throat. In one embodiment, the applicator is a dropper. In another embodiment, the applicator is an aerosol nozzle, either providing a measured or unmeasured dosage of the solution described above.

These and other objects of the present invention will become more readily appreciated and understood from a consideration of the following detailed description of the preferred embodiments when taken together with the accompanying drawings, in which:

BRIEF DESCRIPTION OF THE DRAWINGS

FIG. 1 is a side view in elevation of a first exemplary embodiment of a prior art container suitable for use with the present invention;

FIG. 2 is a side view in elevation of a second exemplary embodiment of a prior art container suitable for use with the present invention;

FIG. 3 is a side view in elevation of a third exemplary embodiment of a prior art container and dropper suitable for use with the present invention; and FIG. 4 is a perspective view of a fourth exemplary embodiment of a prior art container and dropper suitable for use with the present invention.

DETAILED DESCRIPTION OF THE EXEMPLARY EMBODIMENTS

The present invention concerns the management of snoring by the instillation of a composition containing an effective amount of dimethysulfone ($DMSO_2$), also known as methylsulfonylmethane (MSM) through the oral route to contact the orophyrnx. Prior to my U.S. Pat. No. 5,569,679, relief of the snoring condition has not readily responded to pharmacologic treatment. There it was surprisingly found that methylsulfonylmethane dissolved in a pharmaceutically acceptable solvent when administered to saturate the mucous membranes of the nasal passageways acts to reduce the instance of snoring for a time interval for approximately 8–12 hours. The disclosure of U.S. Pat. No. 5,569,679 is incorporated herein by reference.

I have now even more surprisingly discovered that it is not necessary to instill the compounds through the nose so as to saturate the mucous membranes of the nasal passageway to achieve reduction of snoring. More particularly, if the mucous membranes of the orophyrnx, including the uvula, the tonsils and the soft palate, are contacted with sufficient methylsulfonylmethane in solution, a large percentage of persons find snoring relief. Such administration can be directly through the mouth, thus mitigating the burning sensation experienced with nasal instillation. Any disagreeable taste can readily be reduced or eliminated by using flavorings or other food additives.

According to the present invention, then, a method of managing snoring has been developed which comprises the step of instilling a solution orally into a patient's orophyrnx wherein the solution includes a carrier solvent containing an effective amount of methylsulfonylmethane as a solute therein. Preferably, the solvent is distilled water, although any solvent which may dissolve the effective amount of methylsulfonylmethane while at the same time being acceptable for instillation through the mouth. Water and phosphate buffered saline, mixed in a 1:1 ratio (equal proportions) by volume may serve as the solvent as many patients prefer this mixture to plain distilled water. While any suitable amount of methylsulfonylmethane may be dissolved in the solvent up to the saturation level, where the solvent is water, it is preferred that the solution contain between 1% and 20%, by weight, inclusively, of methylsulfonylmethane. A flavoring compound may be included within the solution in order to minimize any unpleasant taste. Such flavoring compound may be selected of any type typically used for pleasant taste, such as menthol, peppermint, spearmint, apple and cherry. The total amount of the composition dispensed should be sufficient to cover the orophyrnx.

The initial experiments to determine effectiveness of the instillation of methylsulfonylmethane as a snoring reduction agent was carried out with an initial sampling of 10 individuals. The empirical data collected for the initial experiment is summarized in the following Table I.

TABLE I

| Subject | Sex | Age | % MSM (by weight) | Results |
|---------|-----|-----|-------------------|---------|
| BW | M | 70 | 15 | MR |
| RS | F | 70 | 15 | FR |
| MS | M | 60 | 15 | FR |
| AD | M | 55 | 15 | NR |
| MD | F | 60 | 15 | NR |
| AW | M | 48 | 15 | FR |
| VS | M | 52 | 15 | FR |
| BJ | F | 60 | 15 | NR |
| HB | F | 64 | 15 | FR |
| JJ | M | 56 | 15 | FR |

FR = Full Relief   MR = Moderate Relief   NR = No Relief

In each of the above cases, the subject was instructed to spray the solution containing the methylsulfonylmethane four (4) times into the oropharynx approximately fifteen (15) minutes to thirty (30) minutes prior to retiring for sleep. Each spray contained about 0.2 ml; to 0.25 ml of the solution. Thus, the total amount instilled is about 0.8 ml to 1.2 ml. The observation of the presence or absence of snoring was made by the subject's mate. The observing party was not told that the subject was employing internasal methylsulfonylmethane. As noted in Table I, 70% of the subject's mates reported the lessening or absence of snoring while 30% reported no benefit from the oral administration of the methylsulfonylmethane.

The seven patients who reported full relief or moderate relief where thereafter provided with a saline spray as a placebo without their knowledge. In each case the snoring returned. They were again given the methylsulfonylmethane spray and 70% again achieve full relief.

A second sampling of subjects was undertaken wherein the weight percentage of methylsulfonylmethane in water was varied at 1%, 5% and 10%. Results of this study is summarized in the following Table II:

TABLE II

| Subject | Sex | Age | % MSM (by weight) | Results |
|---------|-----|-----|-------------------|---------|
| MJ | F | 64 | 1% | FR |
| SO | M | 58 | 1% | NR |
| TJ | M | 60 | 1% | NR |
| WB | M | 79 | 1% | NR |
| BJ | M | 60 | 5% | FR |
| SS | M | 69 | 5% | NR |
| JS | M | 74 | 5% | FR |
| CO | F | 72 | 5% | NR |
| II | F | 78 | 10% | FR |

TABLE II-continued

| Subject | Sex | Age | % MSM (by weight) | Results |
|---------|-----|-----|-------------------|---------|
| TC | F | 76 | 10% | FR |
| WB | M | 69 | 10% | FR |
| MT | M | 70 | 10% | NR |

FR = Full Relief   MR = Moderate Relief   NR = No Relief

While Table II demonstrates that relief of snoring occurred at concentrations of as little as 1% methylsulfonylmethane by weight in water, the relief was not reported to be as dramatic as at higher concentrations.

By warming the solution of water and methylsulfonylmethane to no more than about 37° C. (98.6° F.), a greater concentration of methylsulfonylmethane will go into solution. Accordingly, a third sampling of four subjects employed such a warmed solution, and the results are reported in Table III.

TABLE III

| Subject | Sex | Age | % MSM (by weight) | Results |
|---------|-----|-----|-------------------|---------|
| JD | M | 72 | 20% | FR |
| OW | M | 76 | 20% | FR |
| MM | F | 68 | 20% | FR |
| DZ | F | 70 | 20% | FR |

FR = Full Relief   MR = Moderate Relief   NR = No Relief

From the data derived from these experiments, as tabulated in Tables I–III, it can be generally surmised that concentrations within a range of 1%–20% methylsulfonylmethane by weight in water are effective. Observations indicate that the higher concentrations within this range are the most effective. However, due to the solubility of methylsulfonylmethane in water, the best range for a useful method and product that avoids the need of warming the solution is in the range of 10%–15% methylsulfonylmethane by weight, especially at a ratio of 15%.

With reference to FIGS. 1–4, it should be appreciated that the solution according to the present invention may be administered through a variety of known techniques, and the present invention is also directed to a product that may be used in treating snoring. Here, the product may be in the form of a solution including a solvent for methylsulfonylmethane and an amount of methylsulfonylmethane dissolved therein. This solution is then packaged in a container with the container included a spray applicator or a dropper associated therewith for instilling the solution through the mouth and onto the back of the throat so that it contacts the uvula, the tonsils and the soft palate.

With reference to FIG. 1, a prior art container is shown which is of the type used to spray a metered quantity of solution into the internasal passageway, but it is believed that it would be suitable for injecting a spray through the mount and onto the oropharnyx. In FIG. 1, container 10 includes a bottle 12 for holding the methylsulfonylmethane solution. Applicator 14 includes a metering spray pump 16 activated by a plunger 18. Upon placing the applicator in the mouth, the plunger 18 is depressed toward bottle 12, and a metered quantity of the solution in bottle 12 is ejected through nozzle 20 as a spray which is placed in the mouth, pointed at the back of the throat. When not in use, container 10 is enclosed by means cap 22 (shown in phantom). As noted, the container 10 is of a type known in the prior art for administering a selected metered dosage.

A second prior art container is shown in FIG. 2. Here, container 40 includes a plastic squeeze bottle 42 adapted to hold the fluid to be dispensed. Plastic squeeze bottle 42 communicates with a nozzle 44 that is threaded at 46 to receive a cap 48 (shown in phantom). Here, bottle 42 may be held upright with nozzle 44 positioned in the mouth, pointed at the back of the throat. Upon squeezing, a mist of solution from bottle 42 is ejected through nozzle 44. Alternatively, bottle 42 may be inverted with nozzle 44 in the mouth and the solution administered drop-wise.

FIG. 3, a standard eye dropper-type container 60 is shown which includes a bottle 62 adapted to receive the fluid. Eye dropper 64 is received in bottle 62 and is threadably mounted thereto by cap 66 mounted on threaded neck 68. Eye dropper 64 includes a flexible bulb 70 which may be compressed to remove air therefrom. By immersing tip 72 of pipette portion 74 in fluid, the release of pressure on bulb 70 causes an amount of solution to be drawn into pipette 74. Pipette 74 may then be placed into the mouth and the solution administered in drop-wise manner.

FIG. 4 depicts another prior art container 80 that may be used with the present invention. Here, the container 80 includes a plastic bottle 82 that holds the fluid to be dispensed. Pump assembly 84 includes a cap 86 that threads onto bottle 82, an elongated tube 88 that extends into the interior of bottle 82 and a plunger 90. When plunger 90 is pressed, fluid is pumped by way of tube 88 that is ejected as a mist at orifice 92. Naturally, the pump assembly 84 could be replaced with a spray nozzle and valve if bottle 82 is pressurized.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A method of managing snoring in a person comprising the step of instilling a solution through the mouth and onto the oropharynx of the person wherein said solution includes a carrier solvent containing an effective amount of methylsulfonylmethane as a solute therein.

2. The method according to claim 1 wherein said solvent is water and phosphate buffered saline mixed in a ratio of 1:1 by volume.

3. The method according to claim 1 wherein said solvent is water.

4. The method of claim 1 wherein the amount of methylsulfonylmethane is between one percent (1%) and twenty percent (20%) by weight, inclusively.

5. The method according to claim 4 wherein the amount of methylsulfonylmethane is between ten percent (10%) and fifteen percent (15%) by weight, inclusively.

6. The method according to claim 1 wherein the solution is instilled as spray.

7. The method according to claim 1 wherein the solution is instilled drop-wise.

8. The method according to claim 1 wherein the solution is instilled within one hour before the subject retires for sleep.

9. The method according to claim 1 wherein said solution is instilled in a sufficient quantity to cover the mucous membranes of the person's uvula, tonsils and soft pallet.

10. The method according to claim 1 wherein said solution includes a flavoring compound.

11. The method according to claim 10 wherein said flavoring compound is selected from a group consisting of: menthols, mint flavorings and fruit flavorings.

12. The method according to claim 10 wherein said flavoring compound is selected from a group consisting of: menthol, peppermint, spearmint, apple and cherry.

13. A method according to claim 1 wherein the solution is an aqueous solution flavored with a flavoring compound.

* * * * *